United States Patent
Davis et al.

(10) Patent No.: US 9,255,061 B2
(45) Date of Patent: Feb. 9, 2016

(54) DEHYDROXYLATION OF NITROALCOHOLS TO NITROALKANES

(71) Applicant: ANGUS Chemical Company, Buffalo Grove, IL (US)

(72) Inventors: Paul Davis, Pune (IN); Raj Deshpande, Pune (IN); George David Green, Cary, IL (US); Vandana Pandey, Pune (IN)

(73) Assignee: ANGUS CHEMICAL COMPANY, Buffalo Grove, IL (US)

( * ) Notice: Subject to any disclaimer, the term of this patent is extended or adjusted under 35 U.S.C. 154(b) by 0 days.

(21) Appl. No.: 14/652,681

(22) PCT Filed: Nov. 21, 2013

(86) PCT No.: PCT/US2013/071262
§ 371 (c)(1),
(2) Date: Jun. 16, 2015

(87) PCT Pub. No.: WO2014/099246
PCT Pub. Date: Jun. 26, 2014

(65) Prior Publication Data
US 2015/0329470 A1     Nov. 19, 2015

(30) Foreign Application Priority Data
Dec. 17, 2012   (IN) ............................ 3892/DEL/2012

(51) Int. Cl.
*C07C 205/00* (2006.01)
*C07C 201/12* (2006.01)

(52) U.S. Cl.
CPC .................................. *C07C 201/12* (2013.01)

(58) Field of Classification Search
CPC ............................ C07C 201/12; C07C 205/02
USPC .......................................................... 568/943
See application file for complete search history.

(56) References Cited

U.S. PATENT DOCUMENTS

| | | | |
|---|---|---|---|
| 3,240,823 A | 3/1966 | Bonetti et al. | |
| 3,297,769 A | 1/1967 | Michalski et al. | |
| 4,319,059 A | 3/1982 | Ishibe | |
| 4,861,925 A | 8/1989 | Quirk | |

FOREIGN PATENT DOCUMENTS

GB          0 596 282       12/1947

OTHER PUBLICATIONS

International Preliminary Report on Patentability for PCT/US2013/071262, issued Jun. 23, 2015.
International Search Report and Written Opinion for PCT/US2013/071262, mailed May 23, 2014.

*Primary Examiner* — Jafar Parsa
(74) *Attorney, Agent, or Firm* — Foley & Lardner LLP

(57) ABSTRACT

The present invention provides a process for producing nitroalkanes by dehydroxylation of nitroalcohols. This provides an alternate reaction route for making nitroalkanes, such as 2-nitropropane and its derivatives.

20 Claims, No Drawings

DEHYDROXYLATION OF NITROALCOHOLS TO NITROALKANES

CROSS-REFERENCE TO RELATED APPLICATIONS

This applications is a 371 National Phase Application of PCT/US2013/071262, filed Nov. 21, 2013, which claims priority from Indian application serial number 3892/DEL/2012, filed Dec. 17, 2012, which are incorporated herein by reference in their entireties.

FIELD OF THE INVENTION

The present invention relates to a process for producing nitroalkanes by dehydroxylation of nitroalcohols.

BACKGROUND OF THE INVENTION

Generally, nitroalkanes are useful as solvents, reactants and reaction intermediates in various industries including coatings, paints, inks, adhesives, polymers, resins, etc. For example, nitroalkanes are used as feedstocks to prepare nitroalcohols which can be further reduced to aminoalcohols. In particular, nitromethane ($CH_3NO_2$) is a highly polar liquid often used as a solvent, such as an extraction solvent, a reaction medium, or a cleaning solvent. It is also a reaction intermediate for the production of pharmaceuticals, pesticides, explosives, fibers, and coatings. Another valuable nitroalkane, for example, is 2-nitropropane ($CH_3CHNO_2CH_3$) which is a colorless liquid commonly used as a solvent, chemical intermediate, or starting material to produce other industrially useful compounds. As a solvent, 2-nitropropane is slightly soluble in water and miscible in numerous solvents including most aromatic hydrocarbons, ketones, esthers, and ethers. Thus, it is useful for making inks, paints, adhesives, varnishes, polymers, resins, and coatings. 2-nitropropane is also used in explosives and as a gasoline additive.

Nitroalkanes are produced industrially by contacting propane with nitric acid at high temperatures, such as 350-450° C., which results in a mixed product containing: nitromethane, nitroethane, 1-nitropropane, and 2-nitropropane.

A different process for preparing nitroalkanes is described in U.S. Pat. No. 4,319,059. In this process, an alpha-bromoalkanoic acid is first reacted with an alkali metal nitrite, in the presence of a magnesium ion ($Mg^{2+}$), in an aprotic solvent to form a chelate, which is neutralized with a mineral acid to produce a nitroalkane having one less carbon atom than the reactant bromoalkanoic acid.

No known processes for preparing nitroalkanes by dehydroxylating the corresponding nitroalcohols are known.

Reductive dehydroxylation is known for activated alcohols, e.g., benzylic alcohols. It has not been documented for nitroalcohols such as the 1,2-nitroalcohols.

The ability to produce nitroalkanes from alternative feedstocks, such as, nitroalcohols or nitropolyols, is desirable.

SUMMARY OF THE INVENTION

The present invention provides a dehydroxylation process for preparing a nitroalkane from a nitroalcohol comprising: (A) contacting a nitroalcohol with an iodine catalyst selected from hydroiodic acid and iodine, in a reaction zone, under hydrogen pressure; and (B) heating the reaction zone and contents to a reaction temperature between 50° C. and 250° C. to form the nitroalkane.

In some embodiments, the nitroalcohol is contacted with hydroiodic acid under hydrogen pressure, and the reaction temperature is between 100° C. and 200° C.

In some embodiments, the nitroalcohol is 2-nitro-2-methyl-1-propanol, the reaction temperature is between 100° C. and 160° C., and the nitroalkane produced is 2-methyl-2-nitropropane.

In some embodiments, a metal complex catalyst is also present in the reaction zone and the reaction temperature is between 100° C. and 160° C. In such embodiments, the nitroalcohol may be contacted with iodine under hydrogen pressure, the nitroalcohol may be 2-nitro-2-methyl-1-propanol, and the nitroalkane produced may be 2-methyl-2-nitropropane. The metal complex catalyst may be a rhodium metal complex catalyst.

DETAILED DESCRIPTION OF THE INVENTION

The following terms, phrases and meanings are used hereinafter.

Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of synthetic techniques, definitions (to the extent not inconsistent with any definitions specifically provided in this disclosure), and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, melt index, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the component amounts of the composition and various process parameters such as, without limitation, reaction temperature and pressure.

The term "nitroalcohol" as used herein means a linear or branched organic compound having from 1 to 20 carbon atoms, one or more nitro functional groups ($-NO_2$) and one hydroxyl group ($-OH$). Where the nitro compound has two or more hydroxyl groups, the term "nitropolyol" will be used.

"Catalytic amount" and like terms, when applied to iodine catalysts, mean the amount of iodine catalyst required to promote, at a desired rate, the dehydroxylation reaction of a nitroalcohol to form the corresponding nitroalkane having the same number of carbon atoms as the starting nitroalcohol. The amount will vary dependent upon a variety of factors including, but not limited to, the nature of the reagents, the dehydroxylation conditions, the nature of the catalyst and the like.

Similarly, "catalytic amount" and like terms, when applied to metal complex catalysts, mean the amount of metal complex catalyst required to promote, at a desired rate, the regeneration of hydroiodic acid (HI) from hydrogen and iodine during the aforesaid hydehydroxylation reaction. The amount will vary dependent upon a variety of factors including, but not limited to, the nature of the reagents, the dehydroxylation conditions, the nature of the catalyst and the like.

"Dehydroxylation conditions" and like terms mean the temperature and pressure under which a nitroalcohol is converted to a nitroalkane in the presence of an iodine catalyst (i.e., hydroiodic acid (HI) or iodine ($I_2$)), under hydrogen pressure, with or without a solvent, and with or without a metal complex catalyst. These conditions are dependent upon a host of factors including, but not limited to, the nitroalcohol, which iodine catalyst is present, the reaction temperature, and whether a metal complex catalyst is present, what type and amount are present. Typically the temperature is up to 200° C., such as from 100° C. to 200° C., more typically from 100° C. to 190° C., or even from 120° C. to 190° C. Typically the pressure is 50 psi (345 kPa) to 2000 psi (13,790 kPa), such as 200 psi (1,379 kPa) to 1000 psi (6,895 kPa) or 200 psi (1,379 kPa) to 800 psi (5,516 kPa), or even 500 psi (3,447 kPa) to 1000 psi (6,895 kPa).

The present invention provides a dehydroxylation process for preparing a nitroalkane from a nitroalcohol. More particularly, a nitroalcohol is contacted with an iodine catalyst, such as hydroiodic acid or iodine, under hydrogen pressure, in a reaction zone, which is then heated to a reaction temperature up to 210° C. to form the corresponding nitroalkane by dehydroxylation. Suitable hydrogen pressure is from 50 to 2000 psig (345 to 13,790 kPa), and preferably from 300 to 1000 psig (2,068 to 6,895 kPa).

The iodine catalyst is selected from the group consisting of hydroiodic acid (HI) or iodide ($I_2$). The iodine catalyst is typically present in a molar ratio of nitroalcohol to iodine of from 1:10 to 100:1, such as between 1:2 and 10:1, and preferably between 3:1 and 9:1.

A solvent is not required, but is recommended. Suitable solvents include solvents, such as, without limitation, water, acetic acid, propionic acid, straight chain and branched isomers of butyric, pentanoic, and hexanoic acids, and mixtures thereof. Preferably, the solvent is polar, but this is not required.

The reaction temperature may be maintained by heating the reaction zone for up to 24 hours, preferably up to 12 hours, and more preferably up to 6 hours, but not less than 1 hour, preferably not less than 2 hours, and more preferably not less than 4 hours.

The reaction temperature may be between 50° C. and 250° C., such as between 100° C. and 220° C., or between 160° C. and 220° C., or between 120° C. and 190° C., or between 170° C. and 200° C., or between 100° C. and 160° C.

Where the reaction temperature is lower, such as between 50° C. and 160° C., hydroiodic acid will not be regenerated and, therefore, a stoichiometric excess of hydroiodic acid should be used. At these lower reaction temperatures, with excess hydroiodic acid, the selectivity to nitroalkane will be at or close to 100%, but the conversion rate of the nitroalcohol may be significantly less than 100%, e.g., possibly as low as 20% or 30%. At higher temperatures, such as between 170° C. and 200° C., hydroiodic acid will be regenerated and the conversion rate of the nitroalcohol will be higher, even as high as 95% or greater, however, the selectivity suffers, resulting in a mixed product which comprises the corresponding nitroalkane in lesser proportions than some of the unintended products such as amines and amino-alcohols.

Applicants have not only surprisingly discovered that it is possible to dehydroxylate nitroalcohols and nitropolyols to form corresponding nitroalkanes, under conditions known and applied to produce N-alkylhydroxylamines from nitroalkanes, but they have also learned that addition of a metal complex catalyst to the nitroalcohol-HI/$I_2$ reaction system allows use of lower reaction temperatures between 100° C. and 160° C., such as between 140° C. and 160° C., while increasing nitroalcohol conversion and selectivity to the desired corresponding nitroalkane.

Thus, a metal complex catalyst may be included with the nitroalcohol and iodine catalyst to assist regeneration of hydriodic acid (HI) from hydrogen and iodine ($I_2$) during the dehydroxylation reaction. Suitable metal complex catalyst include, without limitation, metal complexes having the following formula:

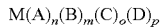

wherein n+m+o+p varies between 4 and 6, and A, B, C or D could be similar or dissimilar ligands, neutral or charged ligands, mono or polydentate ligands having the binding moiety as phosphorus, nitrogen, sulfur, oxygen, or halogen, M could be an element from Rh, Ru, Ir, Ni, Co. Preferred metal complex catalysts are rhodium (Rh) complex compounds, such as $Rh(PPh_3)_3Cl$.

Where present, the metal complex catalyst is present at a molar ratio of metal complex to iodine of between 1:1000 and 1:2, and preferably between 1:50 and 1:10.

The nitroalcohols useful in the practice of this invention may be, without limitation, selected from $C_1$-$C_{20}$ nitroalkanols. Particularly preferred are nitroethanol, 1-nitropropanol, and 2-nitropropanol, derivatives and combinations thereof. For example, without limitation, 2-nitro-2-methyl-1-propanol (2-NMP) would be a derivative of 2-nitropropanol which is suitable for use in connection with the present invention.

It is noted that the dehydroxylation process of the present invention is also useful for converting nitropolyols to nitroalcohols and, then, to nitroalkanes. For example, 2-nitro-2-methyl-1,3-propandiol (NMPD) can be converted to 2-nitro-2-methyl-1-propanol (2-NMP), which can then be further dehydroxylated to 2-methyl-2-nitropropane (2-MNP).

In some embodiments of the dehydroxylation process of the present invention, a nitroalcohol is converted to a nitroalkane in the presence of hydroiodic acid, with a molar excess of hydroiodic acid, at reaction temperatures between 100° C. and 160° C., under hydrogen pressure.

In some embodiments, a nitroalcohol is converted to a nitroalkane in the presence of hydroiodic acid with a molar excess of the nitroalcohol, at reaction temperatures between 170° C. and 200° C., under hydrogen pressure.

In still other embodiments, a nitroalcohol is converted to a nitroalkane in the presence of iodine at a mole ratio of nitroalcohol to iodine of from 1:0.1 to 1:0.5, at reaction temperatures between 100° C. and 160° C., under hydrogen pressure, and in the presence of a rhodium metal complex catalyst.

Various embodiments of the process of the present invention will now be described in detail in connection with the following examples.

EXAMPLES

Key Terminology

2-NP=2-nitropropane
2-NMP=2-nitro-2-methyl-1-propanol

Glacial acetic acid=undiluted or pure acetic acid
HI=hydroiodic acid

General Experimental Procedure

A 300 mL Hast-C Parr reactor was charged with a known amount of 2-NMP (70% in water), glacial acetic acid (80 mL), and hydrogen iodide (55% aqueous w/w Merck) or iodine (equivalent amount S.D. Fine-Chem Ltd). The autoclave was sealed, purged with nitrogen (200 psig) twice, and then pressurized to the desired pressure of hydrogen. Agitation was started and set at 1000 rpm. The reaction temperature was increased to the desired temperature and maintained for the required duration. At the end of reaction the autoclave was cooled to room temperature and a sample was collected for analysis.

Gas Chromatograph Analysis Procedure

The liquid samples were analyzed on Agilent 7890 GC. Agilent HP-5 (19091J-413) GC column (30 m×320 µm×0.25 µm) and the progress of the reaction monitored based on GC area %. The FID (flame ionization detector) was set at 280° C. and the injector port at 180° C. The oven temperature was set at 80° C. and hold for 2 minutes and further to 200° C. with temperature ramping of 10° C./min. The injection volume was 1 µL with split ratio of 25:1 and helium was used as carrier gas.

Example 1

Dehydroxylation of 2-nitro-2-methyl-1-propanol (2-NMP) Using HI

2-NMP (0.011 moles), HI (0.022 moles), T (120° C.), Time (6 hours).

At the end of 6 hours, a 28% conversion of 2-NMP was obtained with 100% selectivity to 2-methyl-2-nitropropane.

Example 2

Dehydroxylation of 2-NMP Using HI

2-NMP (0.011 moles), HI (0.022 moles), T (140° C.), Time (6 hours)

At the end of 6 hours, a 40% conversion of 2-NMP was obtained with 100% selectivity to 2-methyl-2-nitropropane.

Example 3

Dehydroxylation of 2-NMP Using HI

2-NMP (0.011 moles), HI (0.022 moles), T (150° C.), Time (6 hours)

At the end of 6 hours, a 59% conversion of 2-NMP was obtained with 100% selectivity to 2-methyl-2-nitropropane.

Example 4

Dehydroxylation of 2-NMP Using HI

2-NMP (0.011 moles), HI (0.022 moles), T (150° C.), Time (6 hours)

At the end of 6 hours, a 82% conversion of 2-NMP was obtained with 100% selectivity to 2-methyl-2-nitropropane.

Example 5

Dehydroxylation of 2-NMP Using HI

2-NMP (0.026 moles), HI (0.004 moles), T (180° C.), Time (6 hours)

At the end of 6 hours, a 58% conversion of 2-NMP was obtained with 41, 14, 43 and 2% selectivity to 2-methyl-2-propan-2-amine, 2-methyl-2-nitropropane, 2-amino-2-methylpropan-1-ol and 2-amino-2-methyl propyl acetate, respectively.

Example 6

Dehydroxylation of 2-NMP Using HI

2-NMP (0.041 moles), HI (0.015 moles), T (180° C.), Time (6 hours)

At the end of 6 hours, a 79% conversion of 2-NMP was obtained with 36, 20, 41 and 3% selectivity to 2-methyl-2-propan-2-amine, 2-methyl-2-nitropropane, 2-amino-2-methylpropan-1-ol and 2-amino-2-methyl propyl acetate, respectively Example 7

Dehydroxylation of 2-NMP Using HI

2-NMP (0.041 moles), HI (0.024 moles), T (190° C.), Time (6 hours)

At the end of 6 hours, a 96% conversion of 2-NMP was obtained with 22, 19, 25 and 33% selectivity to 2-methyl-2-propan-2-amine, 2-methyl-2-nitropropane, 2-amino-2-methylpropan-1-ol and 2-amino-2-methyl propyl acetate, respectively.

Example 8

Dehydroxylation of 2-NMP Using HI

2-NMP (0.041 moles), HI (0.0079 moles), T (190° C.), Time (6 hours)

At the end of 6 hours, a 92% conversion of 2-NMP was obtained with 44, 15, 38 and 3% selectivity to 2-methyl-2-propan-2-amine, 2-methyl-2-nitropropane, 2-amino-2-methylpropan-1-ol and 2-amino-2-methyl propyl acetate, respectively.

Example 9

Dehydroxylation of 2-NMP Using HI

2-NMP (0.011 moles), HI (0.022 moles), T (150° C.), Time (6 hours)

At the end of 6 hours, a 59% conversion of 2-NMP was obtained with 100% selectivity to 2-methyl-2-nitropropane.

Example 10

Dehydroxylation of 2-NMP Using HI

2-NMP (0.041 moles), HI (0.024 moles), T (190° C.), Time (6 hours)

At the end of 6 hours, a 96% conversion of 2-NMP was obtained with 22, 19, 25 and 33% selectivity to 2-methyl-2-propan-2-amine, 2-methyl-2-nitropropane, 2-amino-2-methylpropan-1-ol and 2-amino-2-methyl propyl acetate, respectively.

Example 11

Dehydroxylation of 2-NMP Using $I_2$

2-NMP (0.031 moles), $I_2$ (0.0098 moles), T (150° C.), Time (6 hours)

Metal Complex Catalyst—Rh(PPh$_3$)$_3$Cl (0.5 g/0.00054 moles)

At the end of 6 hours, a 71% conversion of 2-NMP was obtained with 72% selectivity to 2-methyl-2-nitropropane.

What is claimed is:

1. A dehydroxylation process for preparing a nitroalkane from a nitroalcohol comprising:
   (A) contacting the nitroalcohol with an iodine catalyst selected from hydroiodic acid and iodine, in a reaction zone, under hydrogen pressure; and
   (B) heating the reaction zone and contents to a reaction temperature between 50° C. and 250° C. to form the nitroalkane.

2. The dehydroxylation process according to claim 1, wherein said reaction temperature is maintained for a period of time up to 24 hours.

3. The dehydroxylation process according to claim 1, wherein the iodine catalyst is hydroiodic acid and the reaction temperature is between 100° C. and 200° C.

4. The dehydroxylation process according to claim 3, wherein the nitroalcohol is 2-nitro-2-methyl-1-propanol, the reaction temperature is between 100° C. and 160° C., and the nitroalkane produced is 2-methyl-2-nitropropane.

5. The dehydroxylation process according to claim 1, wherein a metal complex catalyst is also present in the reaction zone and the reaction temperature is between 100° C. and 160° C.

6. The dehydroxylation process according to claim 5, wherein the iodine catalyst is iodine.

7. The dehydroxylation process according to claim 5, wherein the metal complex catalyst is of formula:

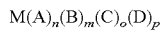

$$M(A)_n(B)_m(C)_o(D)_p$$

wherein n+m+o+p is between 4 and 6;
A, B, C, and D are independently neutral or charged, mono or polydentate ligands having as a binding moiety phosphorus, nitrogen, sulfur, oxygen, or halogen, and
M is Rh, Ru, Ir, Ni, or Co.

8. The dehydroxylation process according to claim 5, wherein the metal complex catalyst is a rhodium metal complex catalyst.

9. The dehydroxylation process according to claim 5, wherein the metal complex catalyst is Rh(PPh$_3$)$_3$Cl.

10. The dehydroxylation process according to claim 6, wherein the nitroalcohol is 2-nitro-2-methyl-1-propanol and the nitroalkane produced is 2-methyl-2-nitropropane.

11. The dehydroxylation process according to claim 1, wherein the pressure is between 50 psi and 2000 psi.

12. The dehydroxylation process according to claim 1, wherein the molar ratio of nitroalcohol to iodine catalyst is 1:10 to 100:1.

13. The dehydroxylation process according to claim 1, wherein the reaction temperature is maintained for a period of time not less than 4 hours.

14. The dehydroxylation process according to claim 1, wherein the reaction temperature is between 100° C. and 220° C.

15. The dehydroxylation process according to claim 1, wherein the nitroalcohol is a C$_1$-C$_{20}$ nitroalcohol.

16. The dehydroxylation process according to claim 1, wherein the nitroalcohol is selected from the group consisting of nitroethanol, 1-nitropropanol, 2-nitropropanol, derivatives thereof, and combinations of any two or more thereof.

17. The dehydroxylation process according to claim 1, wherein the nitroalcohol is 2-nitro-2-methyl-1-propanol and the nitroalkane is 2-methyl-2-nitro-propane.

18. A dehydroxylation process for preparing a nitroalkane from a nitropolyol comprising:
   (A) contacting the nitropolyol with an iodine catalyst selected from hydroiodic acid and iodine, in a reaction zone, under hydrogen pressure;
   (B) heating the reaction zone and contents to a reaction temperature between 50° C. and 250° C. to form a nitroalcohol; and
   (C) continuing to heat the reaction zone and contents to form the nitroalkane.

19. The dehydroxylation process according to claim 18, wherein the nitropolyol is 2-nitro-2-methyl-1,3-propandiol, the nitroalcohol is 2-nitro-2-methyl-1-propanol, and the nitroalkane is 2-methyl-2-nitropropane.

20. The dehydroxylation process according to claim 18, wherein the iodine catalyst is hydroiodic acid and the reaction temperature is between 170° C. and 200° C.; or
   the iodine catalyst is iodine, the reaction temperature is between 100° C. and 160° C., and a rhodium metal complex catalyst is also present in the reaction zone.

* * * * *